United States Patent
Liskin

(12) 
(10) Patent No.: US 8,278,610 B2
(45) Date of Patent: Oct. 2, 2012

(54) RESONANCE CHAMBER, ESPECIALLY FOR AN APPARATUS FOR PASTEURIZATION OF LIQUID PRODUCTS

(75) Inventor: Mikolaj Liskin, Ostroda (PL)

(73) Assignee: Enbio Technology SP.Z.O.O., Kosakowo (PL)

( * ) Notice: Subject to any disclaimer, the term of this patent is extended or adjusted under 35 U.S.C. 154(b) by 0 days.

(21) Appl. No.: 13/059,294

(22) PCT Filed: Dec. 15, 2008

(86) PCT No.: PCT/PL2008/000096
§ 371 (c)(1),
(2), (4) Date: Feb. 16, 2011

(87) PCT Pub. No.: WO2010/027285
PCT Pub. Date: Mar. 11, 2010

(65) Prior Publication Data
US 2011/0142732 A1    Jun. 16, 2011

(30) Foreign Application Priority Data
Sep. 5, 2008    (PL) .......................................... 386028

(51) Int. Cl.
*H05B 6/00*    (2006.01)
(52) U.S. Cl. ........ 219/678; 219/687; 426/237; 426/241; 422/307
(58) Field of Classification Search .................. 422/307; 219/678, 687; 426/237, 241
See application file for complete search history.

(56) References Cited

U.S. PATENT DOCUMENTS

| 4,952,763 | A | 8/1990 | Fritz |
| 5,184,046 | A | 2/1993 | Campbell |
| 6,517,711 | B1 | 2/2003 | Rummler et al. |

FOREIGN PATENT DOCUMENTS

| AU | 629348 | 10/1992 |
| JP | 1202276 A | 8/1989 |
| WO | 96/36246 | 11/1996 |
| WO | 2008/013749 A1 | 1/2008 |

OTHER PUBLICATIONS

International Search Report dated Jun. 2, 2009 in corresponding International Application No. PCT/PL2008/000096.
International Preliminary Report on Patentability, Nov. 23, 2010 in in corresponding International Application No. PCT/PL2008/000096.

*Primary Examiner* — Sean E Conley
(74) *Attorney, Agent, or Firm* — The Law Office of Michael E. Kondoudis

(57) ABSTRACT

The resonance chamber (1) has the form of an elongated closed shape. Microwave generators are fastened to the walls (1.1,1.2) of the chamber (1), their antennae (3,4) directed to the inside of the chamber (1). The microwave generators with antennae (3) are fastened to the chamber wall (1.1), while the microwave generators with antennae (4) are fastened to the wall (1.2) of the resonance chamber. The microwave generators on the wall (1.1) of the chamber are fastened so that in an orthogonal projection into the opposite wall of the chamber the antennae of two neighboring magnetrons are situated on the opposite sides of the product flow conduit (2). The antennae (3) of the successive magnetrons of the first series are situated alternately on the left and on the right side of the product flow conduit (2). Similarly distributed are the antennae (4) of the successive magnetrons of the second row.

5 Claims, 2 Drawing Sheets

Figure 1:
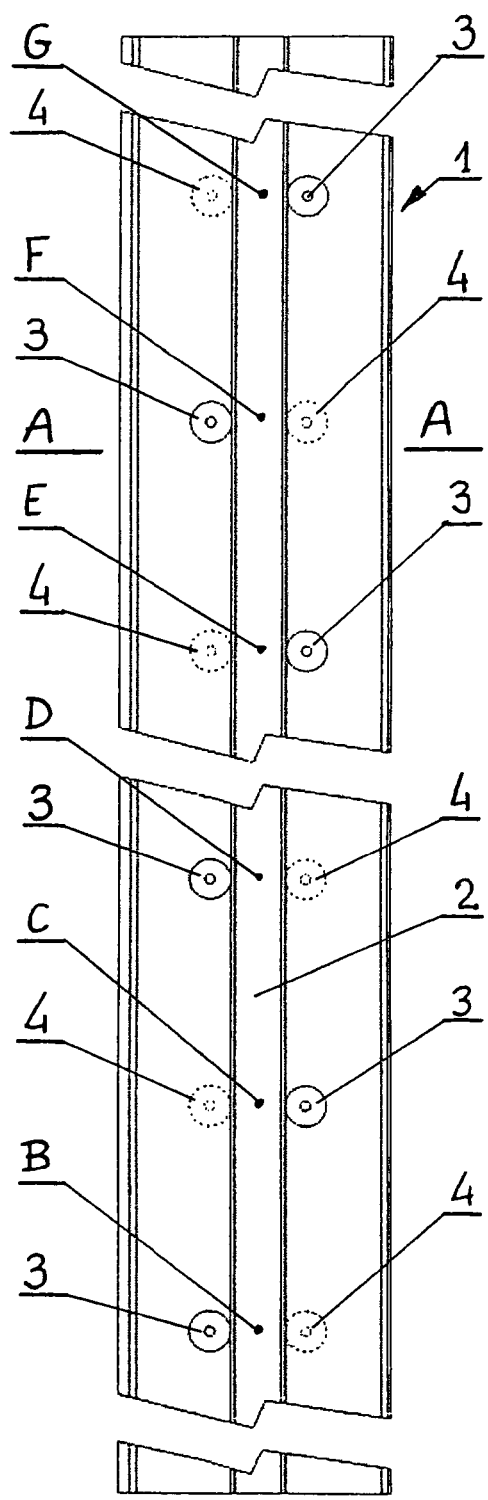

RESONANCE CHAMBER, ESPECIALLY FOR AN APPARATUS FOR PASTEURIZATION OF LIQUID PRODUCTS

A resonance chamber, especially for an apparatus for pasteurization of liquid and semi-liquid products, mainly liquids of diverse densities in the food industry, pharmaceutical industry or other industry fields, is the subject of the invention. In the apparatus according to the invention the microwave radiation energy is used for pasteurization.

Maintaining sterile conditions through elimination of all undesirable microbes and their spore forms from the entire production process is the condition to be fulfilled for conducting a number of industrial processes, as in the food industry, chemistry, pharmacy, as well as for breeding of biological cultures. Purity of the substrates used, but also purity of the products, including liquid substances of various densities is one of the conditions of achieving correct results. In a number of cases the components of the liquids may be favorable for microbe development, if the substrates used, including liquids, have been inaccurately sterilized. For elimination of these hazards it is necessary to adopt pasteurization, aimed at possibly complete sterilization of said liquid or semi-liquid products or substrates for further process engineering operations or packing.

A number of ways and devices for pasteurization of liquid or semi-liquid products are known. Most frequently this process consists in heating of the product. That includes technologies and equipment using radiation, also the microwave radiation in a range from 1 GHz through 150 GHz, to heat products of that kind to the pasteurization temperature.

For situations where the process engineering requirements do not allow the product to contact the heating surface, a number of solutions adopting ultrasounds have been proposed. The invention presented concerns a device, in particular a resonance chamber for heating of a product, especially a fluid, where microwave generators, in particular in the form of magnetrons, are used.

A process of sterilization and pasteurization of dry and liquid products, especially pharmaceutical and food products, with high frequency microwaves is known from an international patent application description No. WO 2008/013449. That known process occurs without heating which might lead to significant physical or chemical changes, resulting in deterioration of the product quality. In said known process the product is exposed to the microwave radiation of frequency and intensity sufficient for penetrating the product in a short time, in principle in one minute or less. In that known solution the suitable frequency for use in typical applications lies in the range from 100 MHz to 110 GHz and the suitable intensity shall approximately be in the range from 100 MHz to 1.6 million watts per $cm^2$. The appropriate time interval for exposition of the product to the microwave environment is not longer than 60 second, a more advantageous interval according to that known solution is 0.001-5 seconds, and the best one is no longer than 1 second.

Another known solution of a device of such kind has been presented in an Australian patent description No. AU 629348. According to that known solution in its most simple form the waves are led along a conductor, formed to have one or more openings on its surface in order to make possible heating of a chosen region of the system. That column is surrounded by a jacket made of a material of low degree of dielectricity, such as Teflon, glass or other appropriate composites or other dielectric materials of sufficiently large losses in the nature, to separate the material to be heated from the wave conductor. The jacket is surrounded by another jacket of dielectric material of low conductivity, which in turn is enclosed with a metal jacket to completely confine those wave conductors. If an appropriate material, such as steel, is used, the subsequent jacket may be omitted. Similarly, the jacket of material of low conductivity, which surrounds the wave conductor, may for some kinds of heated materials be replaced with another weakly conducting barrier, such as air or other gas curtains, meant as separating barriers of low conductivity. According to that known solution the heating microwave system contains a microwave radiation source, a wave conductor containing that source, which enables emission of the microwave radiation from this radiation conductor, containing a material protecting against radiation leakage to the outside and partly surrounding said radiation conductor, into which the material to be pasteurized is led, and containing formed partly from a material reflecting microwaves, for letting to that region the material to be heated and protecting against runout of said microwave radiation. According to that known solution, the method of material heating consists in flowing of the microwave radiation along the radiation conductor and emitting that radiation from the radiation conductor, in one or more positions, to the material subject to pasteurization. Another known solution of the method and apparatus for pasteurization of a flowing product without a hazard of burning has been presented in an international application description No. WO 96/36246. According to that known solution the microwave heating is adopted to gradually increase the fluid temperature up to the pasteurization temperature. It is advantageous to preliminarily heat the fluid to a temperature lower by several degrees from the pasteurization temperature. A heating surface and heat recovery may be used for the preliminary heating of the fluid. In that known solution the apparatus for thermal pasteurization and enzymatic deactivation consists of an inlet unit, preliminary heating unit and microwave heating unit. In an advantageous design the preliminary heating unit contains a heat recovery assembly and a surface heating assembly. The inlet unit contains inlets for liquids to be pasteurized, such as concentrates of fruit juices, milk or biological fluids. It is essential that pasteurization takes place in a chamber, without a hazard of burning of such products. The apparatus contains a unit for preliminary heating of the flowing liquid to a temperature below the pasteurization temperature and a microwave unit for heating the preliminarily heated liquid to the pasteurization temperature, where the microwave unit mounted on the pasteurization chamber emits the microwave energy to the flowing liquid heated preliminarily to a temperature not resulting in burning of the flowing liquid. The degree of preliminary heating protects the liquid against entering the pasteurization temperature range. Several conductors connected together in a spiral configuration are placed in the microwave heating unit, the conductors being transparent to the microwave energy and contained entirely in the microwave unit. The microwave unit contains in that solution at least one source of high frequency microwave radiation and the liquid subject to pasteurization covers a definite distance in that region of intense microwave radiation. Another solution, known from a Japanese patent description No. JP 1202276, presents a continuous process of pasteurization and sterilization of a loose food product. A closed space of a chamber, inside which a worm conveyor made of a heat and pressure resistant material rotates, is placed in the electric field of a high frequency oscillator.

Powdered food is led to the closed pasteurization space and moved under pressure and in the presence of heating by the worm conveyor. Simultaneously the powdered food may be heated, pasteurized and sterilized in a continuous run in a short time without losing its organoleptic values.

According to next another solution, known from a Japanese patent description No. JP 63065251, the liquid to be heated flows at a defined velocity within a plastic conduit. A bundle of microwaves is directed at that conduit. The temperature of the liquid increases inside the conduit section on which the microwave bundle acts. The microwave generator and the section of the liquid flow conduit are enclosed in a chamber preventing a wave run-out.

According to the invention the resonance chamber, especially for an apparatus for pasteurization of liquid products, contains a product flow conduit made of a material transparent to microwaves, and a tight metal enclosure around that conduit. Microwave generators are mounted on the chamber walls, with their antennae directed towards the inside of the chamber.

According to the invention, the chamber is characterized by having the microwave generators mounted alternately on the opposite sides of the chamber walls, each of the two antennae of the generators of a pair of microwave generators having been located in the same section of the product flow conduit. However, the axes of symmetry of each pair of the opposite antennae do not coincide, but are shifted relative to each other. In a solution according to the invention one antenna of each pair of antennae is located on one side of the product flow conduit, and the other antenna of each pair of antennae is placed on the other side of the product flow conduit.

In an advantageous version of the invention each pair of the microwave generator antennae is located inside a resonance chamber, on the level of the same position along the product flow conduit, the microwave generator antenna passing by the product flow conduit wall without touching it. However, it is not excluded that the microwave generator antenna might be tangential to the outer edge of the product flow conduit wall cross-section.

The apparatus according to the invention has been developed in order to optimize performance of pasteurization processes of flowing liquids and semi-liquids under conditions of a lack of contact of the liquid with the heating surface. To this end it has been proposed to place the liquid conduit in the central part of the pasteurization chamber, while the antennae of the microwave generators have been positioned on the walls of that chamber on the opposite sides in such a manner, that on one side of the liquid flow conduit the antenna of a microwave generator is placed on the chamber wall, and at the same height of the chamber on its opposite wall the antenna of the other microwave generator is placed on the other side of the liquid conduit. Below and above this pair of microwave generator antennae there is another pair of microwave generator antennae, situated however on the opposite sides than the first pair of the microwave generators. That has resulted in a substantial progress in development of microwave pasteurizers, where unexpectedly a significant improvement of pasteurization results has been achieved, confirmed by laboratory tests of products subjected to pasteurization in the apparatus according to the invention.

Figure 2:
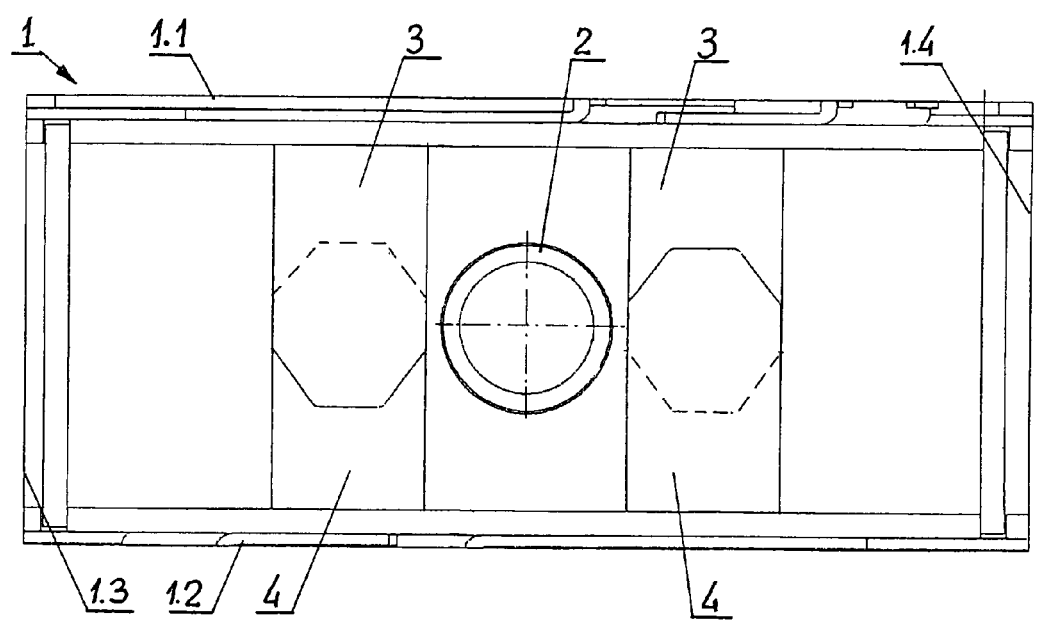

The subject of the invention has been presented in enclosed drawings of an example of implementation, where the respective figures show:

FIG. 1—side view of the resonance chamber,
FIG. 2—A-A section of the resonance chamber As shown in the enclosed drawing FIG. 1 the resonance chamber 1 in the implementation example, serving as a part of an apparatus for pasteurization of liquid products of various densities, has the form of an elongated closed shape. It can be seen in FIG. 2 that the cross-section A-A of the shape has the form of a rectangle. That does not exclude other examples of construction of the resonance chamber 1, for instance as a shape of circular cross-section. However, the figure shows as an example a version having a rectangular section A-A. The apparatus for pasteurization is equipped with known systems of product feeding to the flow conduit inside the resonance chamber and collecting it after pasteurization, and may also be equipped with known systems for preliminary heating of the product prior to pasteurization.

FIGS. 1 and 2 show inside the resonance chamber the product flow conduit 2, made of Teflon as a material transparent for the microwaves. The conduit 2 has a diameter of 30 mm. Other examples of implementation may have the conduit 2 of different diameters. The enclosed drawings FIG. 1 and FIG. 2, show the microwave tight metal housing of the resonance chamber 1 surrounding said conduit.

The longitudinal symmetry axis of the product flow conduit 2 coincides in this example of implementation with the longitudinal symmetry axis of the resonance chamber. These axes may not coincide with each other in other examples of implementation. The walls 1.1, 1.2, 1.3, 1.4, confining the closed space of the resonance chamber 1, are made of a metal material.

In the implementation example shown in FIG. 1 and FIG. 2 microwave generators, that is magnetrons, are fastened to the walls 1.1 and 1.2 of the chamber, and their antennae 3, 4 directed to the inside of the chamber. As shown in FIG. 1 and FIG. 2, microwave generators with antennae 3 are fastened to the chamber wall 1.1, while microwave generators with antennae 4 are fastened to the wall 1.2 of the resonance chamber. To maintain transparency of the figures the antennae placed in the internal space of the resonance chamber rather than the complete magnetrons are shown.

FIG. 1 and FIG. 2, shows that the microwave generators on one wall 1.1 of the chamber are fastened so that in an orthogonal projection onto the opposite wall the antennae of two neighboring magnetrons are situated on the opposite sides of the product flow conduit 2. Thus, as can be seen in FIG. 1, the antennae 3 of the successive magnetrons of the first series are situated alternately on the left and on the right side of the product flow conduit 2.

Shown with dashed lines in FIG. 1 are the antennae 4 of the magnetrons of the second series, positioned on the other, opposite wall 1.2 with a spacing similar to that of the antennae 3 of the first series. As can be seen in FIG. 1 the antennae 4 of the successive magnetrons of the second row are situated alternately on the right and on the left side of the product flow conduit 2.

Each pair of magnetrons of with antennae 3, 4 consists of one magnetron of the first series and one magnetron of the second series. In the implementation example presented in FIG. 1 one pair of antennae 3, 4 is situated at each of the successive points B, C, D, E, F, G of the resonance chamber, i.e. one antenna 3 of the first series is placed on one side of the product flow conduit 2 and one antenna 4 of the second series is placed on the other side of the product flow conduit 2. It can be seen in FIGS. 1 and 2 that the symmetry axes of each pair of opposite antennae 3, 4 at each of points B, C, D, E, F, G do not coincide, but are shifted relative to each other. Points B, C, D, E, F, G are only shown in FIG. 1 to illustrate the positions of the successive pairs of antennae 3, 4, and in that example of implementation their spacing equals 12 cm, but that does not impose restrictions on other implementation examples, where the spacing of these points is different.

In an advantageous version of the invention each pair of microwave generator antennae 3, 4 is situated inside the resonance chamber 1, at a level of the same of points B, C, D, E, F, G, H along the product flow conduit 2. The antennae 3, 4 of the microwave generators passing by the product flow conduit 2 wall without touching that wall. It is, however, not excluded that the antennae 3, 4 of the microwave generators may occupy a position tangential to the product flow conduit 2 wall cross-section.

The invention claimed is:

1. A resonance chamber, especially for an apparatus for pasteurization of liquid products, comprising:
   a liquid product flow conduit made of a material permeable to microwaves;
   a metal enclosure to that surrounds the flow conduit;
   microwave generators, each with an antenna, the microwave generators fastened to the chamber enclosure walls so that the respective antennae (i) are directed inside the chamber and (ii) are arranged in cooperating pairs,
   wherein orientations of the respective pairs of antennae (3,4) of the microwave generators alternate inside the chamber so that
   (1) each pair of antennae (3,4) is situated within a same section of the product flow conduit, and
   (2) respective symmetry axes of each pair of antennae (3,4) do not coincide and are shifted relative to each other, and one antenna (3) of each pair of antennae is placed on one side of the product flow conduit (2), while the other antenna (4) of each pair of antennae is placed on the other side of that product flow conduit (2).

2. The chamber of claim 1, wherein each pair of antennae (3,4) of the microwave generators is situated at a level of the same of point (B, C, D, E, F, G, H) along the product flow conduit (2).

3. The chamber of claim 1, wherein the microwave generator antenna (3,4) passes by the product flow conduit (2) wall.

4. The chamber of claim 1, wherein the microwave generator antenna (3,4) is tangential to the outer edge of the product flow conduit (2) wall cross-section.

5. A resonance chamber, comprising:
   a metal enclosure that is not permeable to microwaves;
   a liquid product flow conduit that is disposed within the metal enclosure; and
   a plurality of microwave generators, each generator having an antenna and attached to a wall of the enclosure so that the respective antennae (i) are directed inside the chamber and (ii) are arranged in cooperating pairs,
   wherein orientations of the respective pairs of antennae of the microwave generators alternate inside the chamber so that:
   (i) each pair of antennae is situated at a same section of the flow conduit,
   (ii) each pair of antennae has a symmetry axis,
   (iii) the symmetry axes do not coincide and are shifted relative to each other, and
   (iv) one antenna of each pair of antennae is located at a first side of the product flow conduit and the other antenna of each pair of antennae is located at a second side of the product flow conduit opposite the first.

* * * * *